(12) United States Patent
Jiang et al.

(10) Patent No.: US 10,357,899 B2
(45) Date of Patent: Jul. 23, 2019

(54) FLEXIBLE MANUFACTURE OF POLYMERIC TUBING INCLUDING FLOW-ALTERING STRUCTURES

(71) Applicants: Fukang Jiang, Arcadia, CA (US); Andrew Dunn, Santa Monica, CA (US); Changgeng Liu, South Pasadena, CA (US)

(72) Inventors: Fukang Jiang, Arcadia, CA (US); Andrew Dunn, Santa Monica, CA (US); Changgeng Liu, South Pasadena, CA (US)

(73) Assignee: MINIPUMPS, LLC., Pasadena, CA (US)

( * ) Notice: Subject to any disclaimer, the term of this patent is extended or adjusted under 35 U.S.C. 154(b) by 842 days.

(21) Appl. No.: 14/818,506

(22) Filed: Aug. 5, 2015

(65) Prior Publication Data

US 2016/0039121 A1 Feb. 11, 2016

Related U.S. Application Data

(60) Provisional application No. 62/033,549, filed on Aug. 5, 2014.

(51) Int. Cl.
C23F 1/00 (2006.01)
C23F 1/02 (2006.01)
(Continued)

(52) U.S. Cl.
CPC ............ B29C 33/52 (2013.01); A61M 5/142 (2013.01); A61M 39/08 (2013.01); B29C 41/02 (2013.01);
(Continued)

(58) Field of Classification Search
CPC .. A61M 5/142; A61M 5/14224; A61M 39/08; A61M 5/14276; A61M 2207/00; B29C 33/52; B29C 41/045; B29C 41/42; B29C 41/02; C23F 1/18; C23F 1/00; C23F 1/02; B29L 2031/753; B29K 2905/10;
(Continued)

(56) References Cited

U.S. PATENT DOCUMENTS

| 4,594,058 A | * | 6/1986 | Fischell | ............ | A61M 5/14224 |
| | | | | | 128/DIG. 12 |
| 4,925,451 A | * | 5/1990 | Amendolia | ....... | A61M 5/16881 |
| | | | | | 137/501 |

(Continued)

FOREIGN PATENT DOCUMENTS

| JP | 2009-112577 A | 5/2009 |
| JP | 2013-220533 A | 10/2013 |
| WO | 2009/137780 A2 | 11/2009 |

OTHER PUBLICATIONS

International Search Report and Written Opinion issued in a corresponding International Application No. PCT/US2015/043810 dated Jan. 4, 2016.

*Primary Examiner* — Lauren P Farrar
(74) *Attorney, Agent, or Firm* — Morgan, Lewis & Bockius LLP (57) ABSTRACT

Tubular polymeric structures are formed by creating a convex mold conforming to a fluid pathway design, depositing a coating of polymer over the mold, and in situ removing the mold without drawing it against the polymer. The resulting structures are fabricated with flow-altering features.

9 Claims, 8 Drawing Sheets (51) Int. Cl.
*C23F 1/18* (2006.01)
*A61M 39/08* (2006.01)
*A61M 5/142* (2006.01)
*B29C 33/52* (2006.01)
*B29C 41/02* (2006.01)
*B29C 41/04* (2006.01)
*B29C 41/42* (2006.01)
*B29K 45/00* (2006.01)
*B29L 31/00* (2006.01)

(52) U.S. Cl.
CPC ............ *B29C 41/045* (2013.01); *B29C 41/42* (2013.01); *C23F 1/00* (2013.01); *C23F 1/02* (2013.01); *C23F 1/18* (2013.01); *A61M 5/14276* (2013.01); *A61M 2207/00* (2013.01); *B29K 2045/00* (2013.01); *B29K 2891/00* (2013.01); *B29K 2901/12* (2013.01); *B29K 2905/08* (2013.01); *B29K 2905/10* (2013.01); *B29L 2031/753* (2013.01)

(58) Field of Classification Search
CPC ............ B29K 2045/00; B29K 2891/00; B29K 2901/12; B29K 2905/08
See application file for complete search history.

(56) References Cited

U.S. PATENT DOCUMENTS

| | | | |
|---|---|---|---|
| 2009/0247982 A1* | 10/2009 | Krulevitch | A61M 5/14224 604/500 |
| 2013/0000119 A1 | 1/2013 | Tai et al. | |
| 2014/0039385 A1 | 2/2014 | Steinbach | |

\* cited by examiner

FLEXIBLE MANUFACTURE OF POLYMERIC TUBING INCLUDING FLOW-ALTERING STRUCTURES

CROSS-REFERENCE TO RELATED APPLICATION

This application claims priority to and the benefit of U.S. Provisional Application No. 62/033,549, filed on Aug. 5, 2014, the entire disclosure of which is hereby incorporated by reference.

TECHNICAL FIELD

The present invention relates to microfluidic channels and methods for their manufacture, and more particularly to conduits capable of accommodating fluid paths with tight radii and varying cross-sections.

BACKGROUND

The need for ever-smaller pumping devices, particularly in the medical field, continues to grow. As a result, the need for increasingly small operational pump components is growing as well, challenging the limits of conventional manufacturing processes. As fluidic devices shrink, it is necessary to manufacture fluidic paths with very tight radii and varying cross-sections to fit within the device package. Some of these cross-sections may not be round, and it may be necessary to form fluidic connectors directly into the fluid paths themselves.

Conventional manufacturing techniques have various limitations. One approach to creating polymeric fluidic paths is to use photoresist to create a channel in a layered polymer. Once the polymer has been layered over the photoresist, it is dissolved to leave a fluid channel; see, e.g., Jason Shih, 2008 "Microfabricated High-Performance Liquid Chromatography (HPLC) System With Closed-Loop Flow Control," Ph.D. thesis, Department of Mechanical Engineering, California Institute of Technology. Another approach is to use polymer extrusion to create small fluid channels; see, e.g., Lopez, Fernando L., 2011, "Micro-Sized Components for Medical Extrusion," Interface Catheter Solutions, California, USA. This is a standard method of fabrication for catheters and other macro-scale tubes. Although varying interior diameters and wall thicknesses are achieved by manipulating extrusion speed and die configurations, shapes such as tight-radius twists and bends are not easily replicable. A third approach is three-dimensional (3D) wax printing to create other types of structures for use in devices. This approach has been used to create relatively large 3D structures coated with very thin polymer layers; see, e.g., Feng, Guo-Hua and Kim, Eun Suk, 2003, "Universal Concept for Fabricating Micron to Millimeter Sized 3D Parylene Structures on Rigid and Flexible Substrates," The Sixteenth Annual International Conference on Micro Electro Mechanical Systems, 2003, pp. 594-597.

Unfortunately, conventional approaches such as these do not readily allow for the creation of fluid paths of a tortuous nature, having varying radii and minute dimensions, and with a smooth finish as necessary for long-term use, especially in implantable drug pumps. Smooth fluid paths within an implantable drug pump are generally necessary to avoid or minimize structures that promote drug aggregation, to reduce clogging, and to avoid long-term biofouling. A particular challenge in conventional manufacturing techniques is integrating flow-altering structures such as filters into a fluid path.

SUMMARY

Manufacturing techniques in accordance herewith are capable of creating a wide array of fluidic paths that meet demanding design criteria and feature integral flow-altering structures. Although the following discussion focuses on parylene (poly(p-xylylene)), it should be understood that the invention is applicable to many polymer systems, particularly those applied by vapor deposition, as will be apparent to those skilled in the art. Embodiments of the invention feature flow-altering structures integral with (e.g., terminating) tubular conduits, as well as flow-altering structures to which a tubular conduit may bond.

In one aspect, the invention pertains to a method of forming a tubular polymeric structure. In various embodiments, the method comprises the steps of forming a convex mold conforming to a fluid pathway design, the mold being formed of a material soluble in a solvent; depositing a coating of polymer over the mold to form a coated structure, the parylene being unaffected by exposure to the solvent; in situ removing the mold by subjecting the coated structure to the solvent; and creating a flow-altering structure at the closed end. In some embodiments, the material comprises or consists essentially of wax, whereas in other embodiments, the material comprises or consist essentially of a thermoplastic. The polymer may, for example, be parylene. The method may further include trimming one or more ends of the tubular polymeric structure to expose a lumen thereof.

In various embodiments, the mold is formed by 3D printing. For example, the mold may be formed into a block of support wax, in which case the method may further comprise dissolving the support wax but not the wax mold. In general, following deposition of the polymer, the mold is dissolved with a solvent that does not dissolve the polymer.

In various embodiments, prior to deposition of the polymer, the molds undergo a smoothing process. The smoothing process may, for example, comprise or consist essentially of passing a solvent vapor over the mold. Alternatively, the smoothing process may comprise or consist essentially of spin coating and baking photoresist over the mold. In still another alternative, the smoothing process may comprise or consist essentially of spray coating polyvinyl alcohol over the mold.

In some embodiments, the flow-altering structure comprises a plurality of apertures through the closed end to permit filtered fluid communication with a lumen of the tubular polymeric structure. The flow-altering structure may be created by steps comprising (i) applying to the closed end a photoresist mask patterned to surround intended locations of the apertures and (ii) creating the apertures at the locations by etching, e.g., reactive-ion etching. Alternatively, the flow-altering structure is created by laser drilling or mechanically drilling the apertures. In the former case, a laser-resistant mask may be disposed on the closed end; the mask is patterned to surround intended locations of the apertures, so that the laser beam penetrates only through the intended aperture locations.

In alternative embodiments, the method comprises forming a tubular polymeric structure according to steps comprising bending a wire to conform to a fluid pathway design; depositing a coating of polymer over the wire; in situ removing the wire without drawing it against the polymer, which releases the tubular polymeric structure; and creating a filter structure at a closed end of the tubular polymeric structure.

In some embodiments, the wire is copper and the removing step comprises etching away the wire by exposure of the coated wire to an etchant; for example, the etchant may be ferrite chloride. In some embodiments, the wire is made of a metal having a melting point lower than the melting point of the polymer (which may, for example, be parylene). For example, the wire may be Field's metal. The method may further comprise the step of shaping a cross-section of the wire prior to the depositing step.

In some embodiments, the flow-altering structure comprises a plurality of apertures through the closed end to permit filtered fluid communication with a lumen of the tubular polymeric structure. The flow-altering structure may be created by steps comprising (i) applying to the closed end a photoresist mask patterned to surround intended locations of the apertures and (ii) creating the apertures at the locations by etching, e.g., reactive-ion etching. Alternatively, the flow-altering structure is created by laser drilling or mechanically drilling the apertures. In the former case, a laser-resistant mask may be disposed on the closed end; the mask is patterned to surround intended locations of the apertures, so that the laser beam penetrates only through the intended aperture locations.

In still another aspect, the invention pertains to a method of fabricating a drug pump. In various embodiments, the method comprises the steps of forming a drug pump including a fluid reservoir and an ejection mechanism for forcing fluid therefrom; forming a plurality of apertures through a wall of the reservoir; and bonding a tubular conduit to the wall of the aperture such that a lumen of the conduit surrounds the apertures, actuation of the ejection mechanism forcing fluid from the reservoir and through the conduit via the apertures so as to filter the fluid.

Yet another aspect of the invention relates to an implantable pump. In various embodiments, the implantable pump comprises first and second walls forming a chamber therebetween, the first wall being expandable so as to vary a volume of the chamber; a plurality of apertures through the second wall of the chamber; an ejection mechanism for selectively expanding the first wall; and a cannula bonded to an exterior face of the second wall such that a lumen of the cannula surrounds the apertures. Actuation of the ejection mechanism forces fluid from the chamber and through the cannula via the apertures so as to filter the fluid.

As used herein, the term "substantially" or "approximately" means ±10% (e.g., by weight or by volume), and in some embodiments, ±5%. The term "consists essentially of" means excluding other materials that contribute to function, unless otherwise defined herein. Nonetheless, such other materials may be present, collectively or individually, in trace amounts.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing will be more readily understood from the following detailed description of the invention, in particular, when taken in conjunction with the drawings, in which.

DETAILED DESCRIPTION

1. Wire Mandrel Method

In one embodiment, a method of tube manufacture utilizes a metal (e.g., copper) wire to fabricate fluid paths with very good control of interior (lumen) dimension and excellent surface finish. In a representative embodiment, the process starts by cutting a length of copper wire having a diameter equal to that of the intended tube inner diameter (ID). The length of the cut copper wire is typically much longer than the length of tube being fabricated. If desired, the wire may be shaped using a pressing tool such as a jig that has been machined to correspond to the desired lumen geometry of the tube. For example, a wire with a round cross-section may be pressed in a jig so that its cross-section is a triangle, square or other polygon. Of course, any suitable machining (or other mechanical) technique may be used to shape the wire, and indeed, wire having a desired cross-sectional shape and diameter may be obtainable commercially. Furthermore, other metals including platinum, tungsten, silver, and various alloys may be used in lieu of copper, but copper is preferred because the copper and ferrite chloride reaction does not generate gases as a byproduct. This makes etching easier without an additional process or the need to remove the gas generated by etching, which is inconvenient and may operate to inhibit the etching process.

The wire with the required cross-sectional geometry may be bent into a shape corresponding to the desired fluid routing path. The wire is then placed in a parylene deposition chamber and a layer of parylene of desired thickness (e.g., 20 μm) is deposited thereon, for example, by vapor deposition. After deposition, the parylene-coated wire is trimmed of polymer at both ends to expose the copper. The trimmed, coated wire is then placed in a solution that will dissolve the wire without harming the polymer coating; for example, in the case of a copper wire, a ferrite chloride solution can be used, typically requiring up to 3 weeks to fully remove the copper. At the end of the etching process only the parylene tube remains. The parylene tube may then be trimmed to the proper length for use.

This method allows for the creation of tubing with highly accurate internal dimensions as wire with a specifically engineered cross-section and consistent cross-section is used in the process. In addition, since the wire may have excellent surface finish, the resulting tube will have very smooth inner surfaces. Unlike extrusion, this method results in a rigid tube that is shaped to conform to the desired fluid path (as opposed to having to shape a straight tube). It may also create a tube with a round cross-section, which facilitates easy fluidic connections. The copper wire may be pre-machined to different cross-sectional shapes or varying radii to create further intricate structures including flow restrictions and grooves for trapping sediment or drug aggregate.

In a variation of this approach, the wire is made of a bismuth, indium, and tin alloy (generally 32.5% Bi, 51% In, and 16.5% Sn) called a Field's metal. This soft metal can be shaped arbitrarily, but melts at 62° C. Accordingly, instead of using a chemical solution to remove the metal, the parylene-coated wire can be heated to the melting point of the metal, which will simply flow out of the tube. Once again, the wire may be pressed into a jig to give the wire the proper geometry, and following polymer deposition, the wire is clipped at both ends to allow the metal to flow out in the next step. A fixture may be used for accurate trimming. The coated wire is placed in an oven set for 62° C. and oriented upright. When the metal reaches 62° C. it melts, leaving only the polymer outer coating behind. The polymer tube is then trimmed to length for use.

This method creates tubing with a highly accurate internal diameter as wire with known tolerance is used in the process. In addition, since the wire has excellent surface finish, the resulting tube has very smooth inner surfaces. Unlike extrusion, this method results in a rigid tube that is shaped to the proper routing as opposed to having to affix a straight tube in the proper orientation. It can be used to create a tube with a round cross-section, which makes fluidic connections very easy to make. Unlike the copper wire method, the wire removal time is a matter of hours as opposed to weeks.

2. 3D Mandrel Method of Tube Manufacture

A second manufacturing technique uses a material, such as wax, soluble in an organic (typically nonpolar) solvent as a 3D printing material to build a convex mold or scaffold onto which a controlled-thickness layer of a polymer such as parylene C is deposited; the polymer is unaffected by the solvent. As used herein, the term "wax" refers broadly to any lipid compound (or mixture of compounds) that is solid at room temperature. Typically, the molecular structure of a wax consists of or comprises long alkyl chains that may or may not have functional groups, and that may include intrachain linkages such as ester linkages Waxes may be natural or synthetic, and may be a single component or a blend of components. Furthermore, other materials such as thermoplastics or organic mixtures may be used as the printing material so long as they are soluble in a suitable solvent. While the ensuing discussion refers to wax for ease of explanation, it should be understood that these alternative materials may be used instead.

The geometry and cross-section of the structure may be created by building up layers of wax to create any arbitrary shape. Following deposition of the parylene onto the mold, the wax is dissolved, leaving only the outer layer of deposited parylene. The result is a tube of controlled wall thickness and accurately controlled cross-section and geometry.

The wax scaffold may be formed in any suitable manner, including, without limitation, molding, extrusion, or selective, layer-by-layer deposition onto a surface in a manner that builds up a 3D structure—a process often termed "3D printing." This wax-scaffold approach to tube fabrication allows for the manufacture of parylene tubes of arbitrary cross-section and routing with very accurate dimensional control. In a representative embodiment, illustrated in FIG. 1A, a 3D wax printer is used to build up the wax scaffold within a block of support wax. The shape and size of a desired cross-section 100 is defined, and a series of flat, elongated wax layers 110 (e.g., having a thickness of 6.35 µm) is sequentially deposited. The layers 110 may follow a tortuous path but along the dimension of deposition roughly conform, collectively, to the cross-section 100—that is, the layers 110 fit as snugly as possible within the envelope defined by the cross-section 100.

Figure 1A:
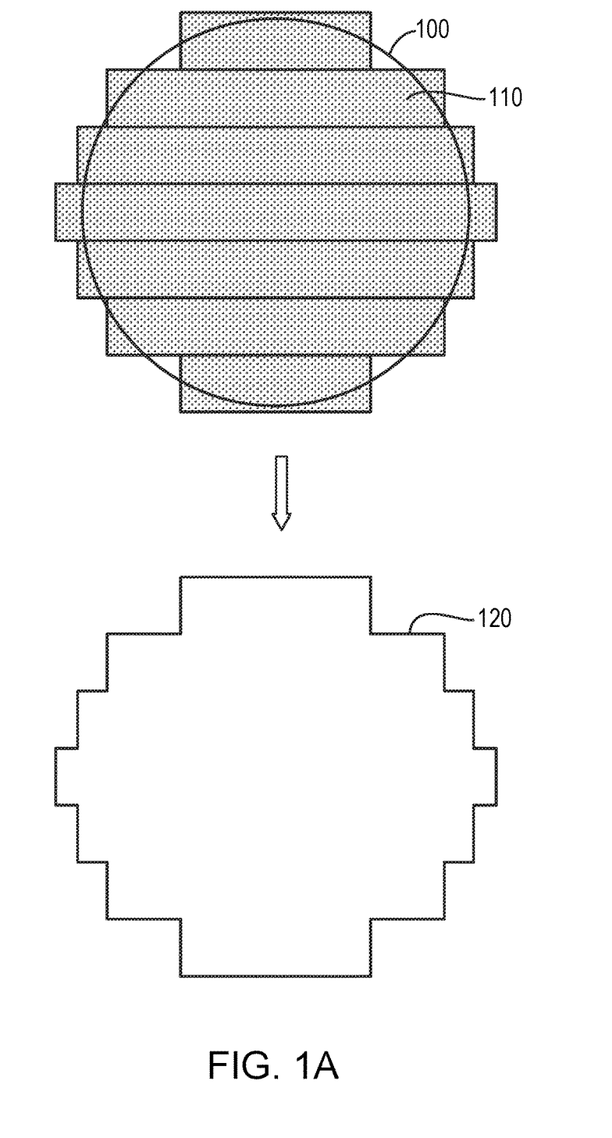
FIG. 1A illustrates the results of a layered fabrication process for forming tubes in accordance with one embodiment.

Once printed, the resulting wax tube mold 120 has a rough and stepped appearance from the layered addition of wax material during the printing process. This can cause the subsequently deposited polymer to be rough and opaque in appearance. To improve the surface finish, a smoothing process is desirably performed on the printed wax molds. One such method is using a solvent vapor such as acetone to smooth the tube molds. Using a convective air current to pass a solvent vapor over the molds, the top layer of wax is softened and reflows over the surface. The resulting mold surface finish is smooth without loss of the material.

The support wax melts at a lower temperature than the deposited wax—for example, the support wax may be a wax mixture (e.g., a naturally produced wax) while the deposited wax may be paraffin. The support block retains the printed wax parts as they are built up in order to prevent them from breaking apart prior to completion. Once the printing is complete, the structure is heated to a temperature sufficient to melt the support wax but low enough to leave the printed wax unaffected (or, alternatively, the structure is subjected to a solvent that dissolves the support wax but not the deposited wax). For example, certain forms of bee's wax melt at 30° C., paraffin may melt at approximately 55° C., and synthetic waxes may have melting points as high as 75 ° C. Using readily available equipment, 3D printing can be controlled to an accuracy of 25.4 µm and can fabricate a minimum feature size of 254 µm; suitable 3D printers include the SOLIDSCAPE T76Plus device marketed by Solidscape Inc., Merrimack, N.H. and the ProJet 3500 series of devices marketed by 3D Systems, Inc., Rock Hill, S.C. The support block may itself be printed or may instead be molded in the form of a block with a recess, the bottom surface of which receives the deposited wax.

An alternative smoothing technique for the wax tube molds utilizes a microelectromechanical system (MEMS) approach. First, a photoresist such as SU-8 is spin-coated onto the printed wax molds. The solvent in the photoresist acts to dissolve away any defects while the resist itself helps to fill the surface steps in the wax mold. Several iterations of the spin coating may be required to achieve the final desired surface finish. The resist is then baked on the molds to evaporate the solvent and harden the resist. This step creates an even surface finish over the entire mold surface while maintaining the shape and size of the tube mold.

In specific applications, it may be desired to create a slightly smaller-diameter tube. By increasing the solvent composition, concentration, or spin coating time, the wax tube may be reduced in size in a controlled fashion by, for example, 5% or 10%. Such an approach can beneficially reduce the size of the tube to dimensions below the capability of the wax printer while also smoothing the surface. For example, a 200 µm diameter structure may be out of the range of the wax printer, which produces (for example) a 230 µm structure with a rough surface of 10 µm. By increasing the photoresist contact duration, the wax mold can be smoothed and reduced to obtain the target 200 µm diameter structure.

The second step addresses the opacity of the parylene after deposition. After spinning and baking the SU-8 photoresist, a thin layer of polyvinyl alcohol (PVA) solution may be sprayed on the photoresist coated molds. The PVA gives a shine to the molds that causes the deposited parylene to be transparent. Several coats of PVA solution may be required to achieve the desired shine on the wax molds.

The smoothing process may also be used for extra dimensional control of the wax molds when, once again, the required dimensions or tolerances cannot be created or maintained by the wax printer itself. Allowing the SU-8 photoresist to remain on the surface of the mold before baking for a longer time period will reduce the size of the mold features. This facilitates incorporation of features that are smaller than the minimum size achievable using available 3D printing technology. Increasing the time the SU-8 photoresist remains on the mold during spinning from 10 up to 20 seconds decreases the feature size by 10%-15% from the 3D printed dimension. By adjusting this spin time, very accurate dimensional changes and control can be achieved.

Once the mold is smoothed, it is placed in a parylene deposition chamber in which a controlled thickness (e.g., 20 µm) of a polymer (e.g., parylene C) is deposited on the surface. After parylene deposition, the ends of the resulting tubular structure are clipped to expose the wax on each end to the outside environment. A fixture may be used for accurate trimming. The structure is then placed in acetone or another other suitable solvent to dissolve away the wax mold from the inside. After 24-48 hours of soak time in acetone, only the parylene outer layer remains.

Figure 1B:
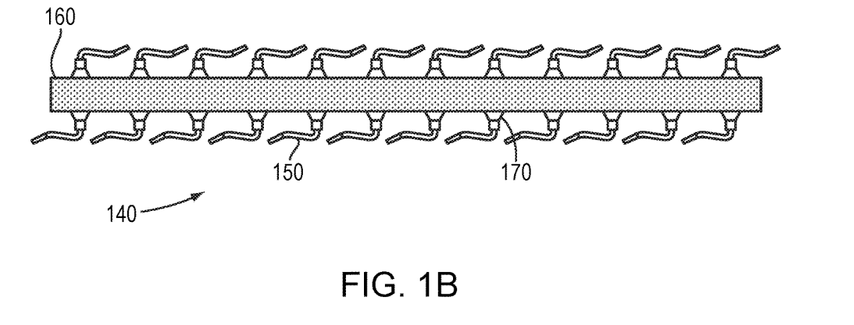
FIG. 1B shows a scaffold for production of multiple similar fluid conduits in a single manufacturing sequence.

Unlike other tube manufacturing methods, 3D printing as described herein easily allows for production of tubes of virtually any shape, diameter, and routing. FIG. 1B illustrates how a single scaffold 140 may be used to create a plurality of tubes in a single batch run without additional handling. The molds 150 for the individual tubes may each be anchored to the scaffold 160 by a mold segment 170 that produces a fludic connector. In use following fabrication, the fluidic connector is used to connect the tubing segment to a conduit (e.g., another tubing segment). The fluidic connector may have a specific cross-sectional geometry (e.g., off-round, polygonal, etc.) to align and connect the tube to an adjacent conduit.

The connector portion typically has a wider diameter than the tube, which serves to sturdy the point of attachment to the scaffold 160, and in some embodiments, the mold segments 170 flare where they are joined to the scaffold 160 in order to increase the surface area of contact with the scaffold and provide further sturdiness to the mold, thereby avoiding inadvertent removal of the molds during manufacture. The flared segment may or may not be part of the finished tube; that is, it may be cut away from the connector or represent a part of it. For example, a conically flared connector portion can provide stress relief when the tube is connected to another conduit.

Following polymer application and cure, the resulting polymer tubes may be cut away from the scaffold 160, and the distal end of each tube may be removed to expose the lumen. The tubes may be subjected to the action of a solvent at this point, but in some embodiments, this occurs while the molds 170 are still adhered to the scaffold 160, which resists the action of the solvent that removes the molds 150 (and so can be re-used). The wax printing method for tube production provides highly accurate tubing structures with minimal manual handling and manufacturing.

3. Solid Manifold Method of Tube Manufacture

Figure 2:
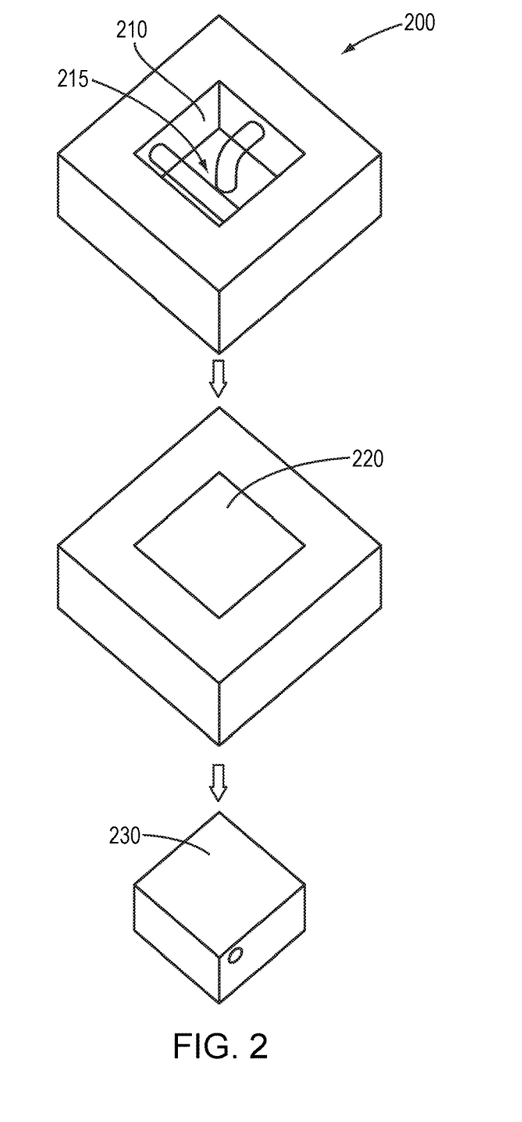
FIG. 2 illustrates fabrication of a solid manifold containing a fluid path in accordance with one embodiment.

The present invention may be used to form a solid manifold with internal fluid paths. A solid manifold is critical for some microfluidic configurations (e.g., modular designs assembled from interchangeable fluid-path components), and more generally offer increased tubing strength, ease of handling, and ease of component integration. By utilizing the flexibility of wax printing technology, manifolds of nearly any configuration can be made. A representative fabrication sequence is shown in FIG. 2. First, a wax mold 200 is printed, molded or otherwise fabricated with an internal cavity 210. Within the cavity 210, a wax structure corresponding to the desired tubing configuration(s) 215 is printed. Next, the cavity 210 is filled with a liquid form of the material that will compose the manifold, e.g., a curable polymeric material such as parylene, silicone or epoxy. After the material 215 is cured (e.g., by exposure to actinic radiation or e-beam, or simply by allowing it to dry and harden), the wax is removed from the finished structure to create the solid manifold 230 containing internal microfluidic passages complementary to the wax structure 215. The wax may be removed from the manifold 230 by heating it to the melting point of the wax and allowing to flow out of the manifold (assisted by an air jet if needed), or by subjection to a solvent for the wax. The more the manifold is cross-linked, the greater will be useful range of solvents, since few solvents will harm a fully cross-linked polymer. The original wax mold 215 may contain additional structural features (pins, slots, indents, partial tubes, grooves, etc.) to help align and connect the tube set with an adjacent component during component integration.

4. Branched Tube Manifold Method of Tube Manufacture

Figure 3:
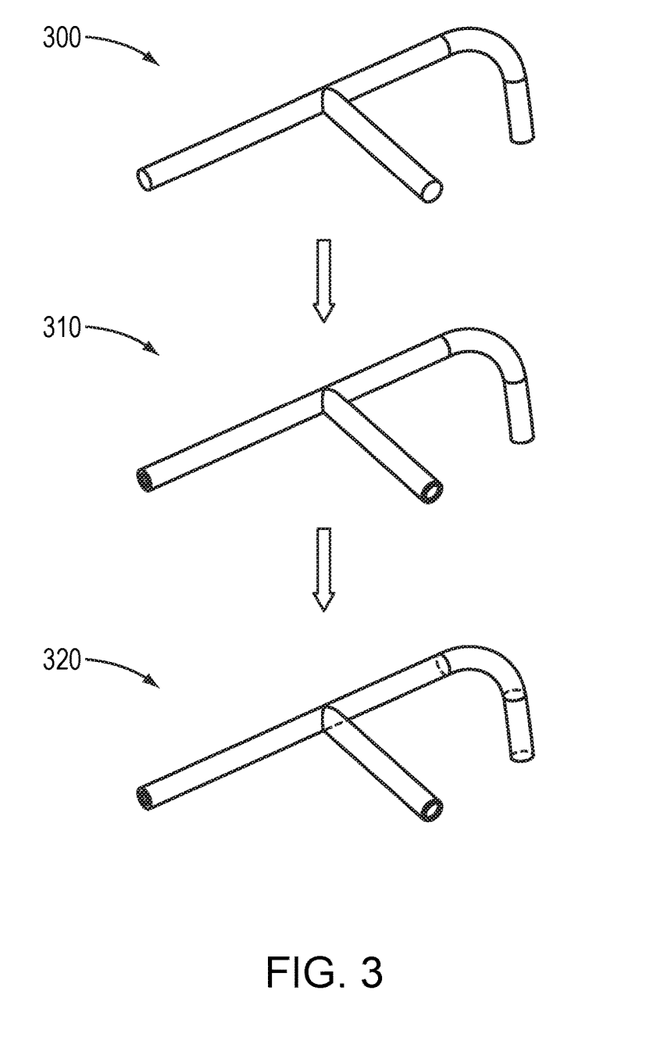
FIG. 3 illustrates fabrication of a branched-tube manifold in accordance with one embodiment.

As illustrated in FIG. 3, a branched tube manifold may be created to consolidate the number of connections as well as reduce the space required for fluidic connections. In a representative fabrication sequence, a wax mold 300 with extensions along multiple fluidic paths is molded or printed. The surface of the wax mold 300 is preferably smoothed as described above. Next, the wax mold is coated with a polymer such as parylene to form a coated structure 310. Finally, the wax mold is heated or dissolved away, leaving parylene tubing 320 conforming to the fluid path defined by the mold 300.

5. Incorporation of Filters, Flow Regulators, and other Flow-Altering Structures Depending on fluid-pathway design constraints, fluid actuation mechanisms, and the fluids that will flow through such pathways, the above-described designs may benefit from the incorporation of filters and flow regulators into fluid paths themselves. In embodiments incorporating one or more check valves, it may be advantageous to place fluid paths having varying radii (or multiple branched fluid paths) to alter the cross-section of specific flow paths—e.g., to alleviate any potential surge in flow that would occur downstream immediately after the cracking pressure of a check valve is reached. Filters may be incorporated along any portion of the fluid path but are desirably placed in areas where they may be flushed periodically to prevent drug aggregate accumulation and possible obstruction of the flow path.

Figure 4A:
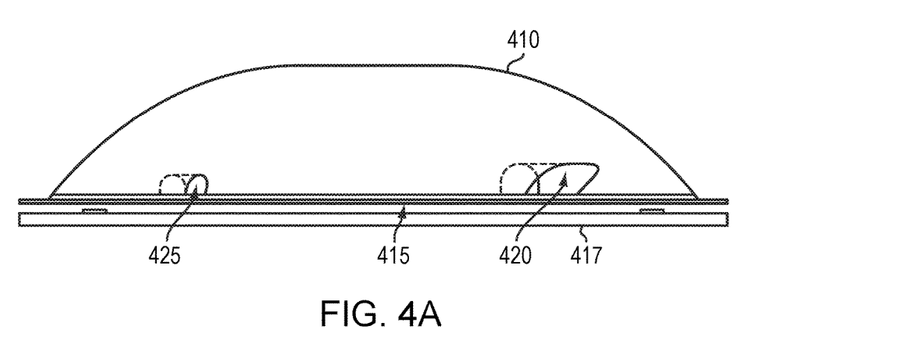
FIGS. 4A-4C illustrate a drug reservoir in elevational, exploded, and sectional views, respectively.
Figure 4B:
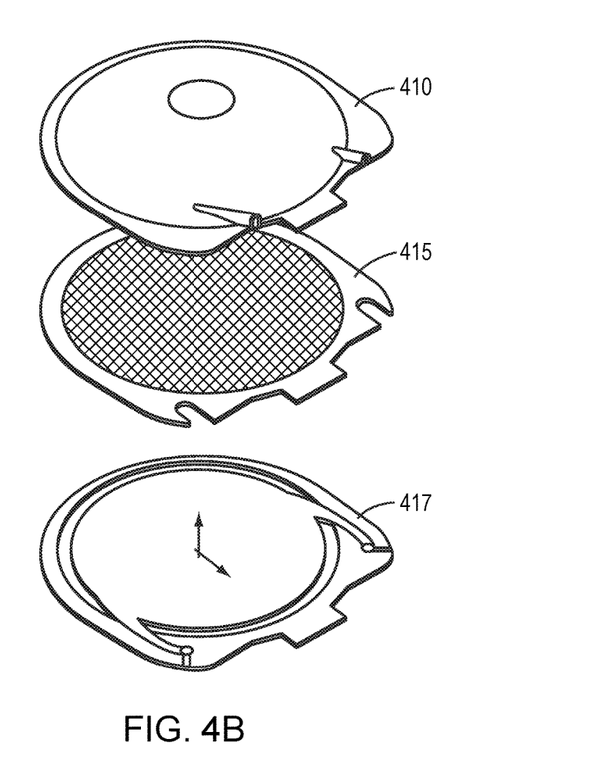
Figure 4C:
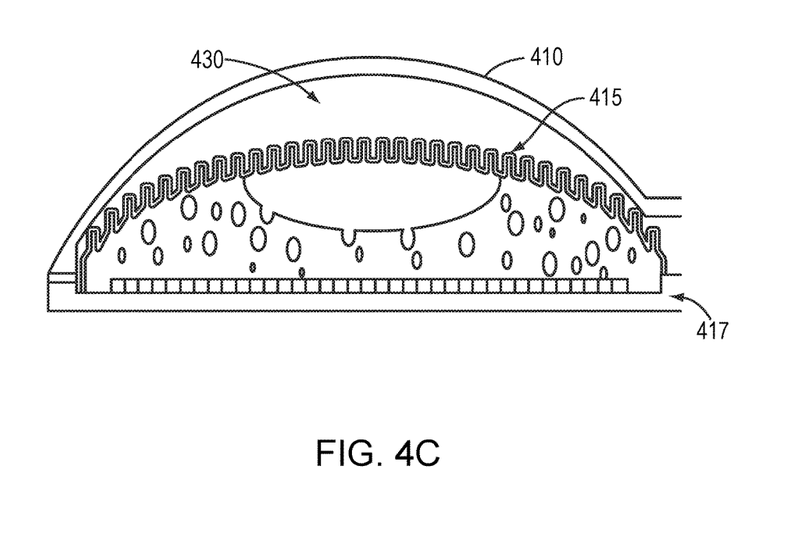

The description that follows will generally focus on devices having small footprints, specifically an electrolysis-actuated, implantable drug-delivery pump as described, for example, in U.S. Pat. No. 8,231,608, the disclosure of which is hereby incorporated by reference. In this embodiment, one location for the filter is in the fluidic pathway to be connected to the drug reservoir (i.e., the chamber created between the top layer and flexible diaphragm in embodiments described in the '608 patent). FIGS. 4A-4C illustrate the drug reservoir of a representative pump in elevational, exploded, and sectional views, respectively, the latter schematically depicting actuation. The drug reservoir is created between a dome-shaped top member 410 and a bottom member 415 that includes a flexible diaphragm; upon joinder thereof along a peripheral edge, a drug reservoir is formed between the members 410, 415. A floor 417 underlies the the diaphragm 415 and includes electrolysis electrodes and circuitry as described in the '608 patent. There are at least two fluid access points to the top member 410 of the drug reservoir: a first access point 420, representing the entrance to a refill port, and a second access point 425, which is connectable to a cannula leading to a site of drug administration within the patient. Both of these access points 420, 425 are molded into the top member 410 and admit a tubular conduit such as a cannula. Again, the drug reservoir 430 is formed between the dome-shaped wall of the top member 410 and the expandable diaphragm or wall 415. Other embodiments may have more than two fluid access locations according to requirements such as fill time, number of cannulas connected to target tissue regions, and number of reservoirs requiring independent fluid access. As illustrated in FIG. 4C, when the electrolysis engine is actuated, electrolysis gas is generated beneath the flexible diaphragm 415, deflecting it to apply pressure to the drug reservoir 430 and thus forcing liquid drug out of the drug reservoir 430 and to the site of administration.

Figure 5A:
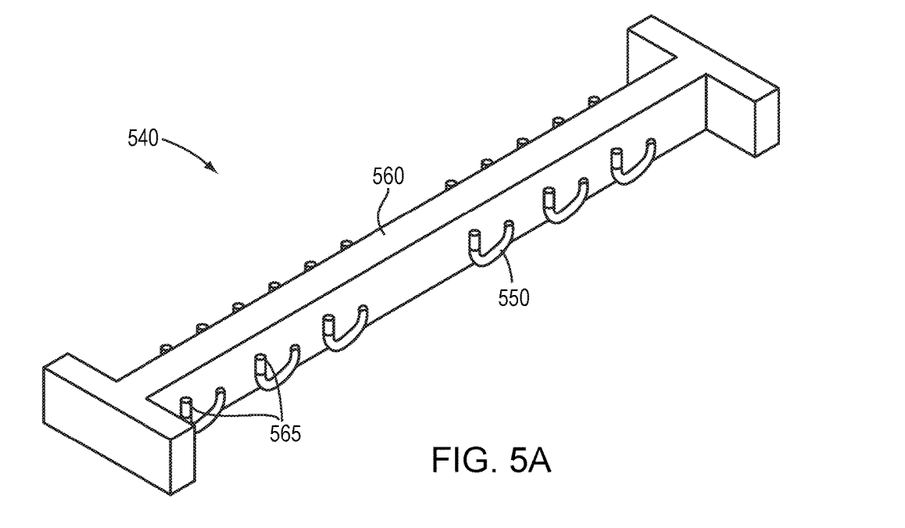
FIG. 5A illustrates a scaffold for production of multiple polymeric tubings with filters integrated.
Figure 5B:
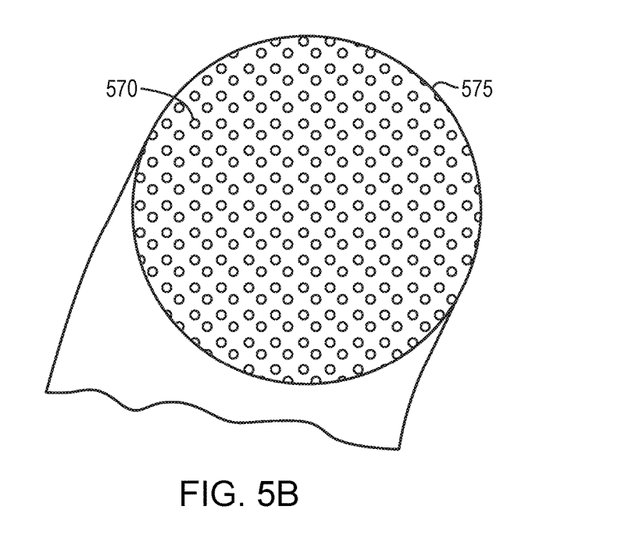
FIG. 5B illustrates a close-up of a filter configuration on the end of a polymeric tubing with 5-micron holes with a 20-micron spacing.

FIGS. 5A and 5B illustrate an embodiment of the polymeric tubing with a filter integrated into the flow path—specifically, at the terminus of a tube segment. FIG. 5A illustrates a scaffold 540 for production of multiple similar fluid conduits utilizing the 3D mandrel method of tube manufacture described earlier, although it should be understood that any of the foregoing production techniques are amenable to augmentation to produce flow-altering structures. The molds 550 for individual tubes may each be anchored to the scaffold 560. When the tubes are separated from the scaffold 560, one terminus of each of the tubes, which during molding overlay the terminal faces 565 of the molds 550, is closed. A pattern 570 of apertures or holes is formed in the terminal faces 575 of the tubes. The apertures 570 are sized to provide a desired degree of filtration or flow alteration. For example, the apertures 570 may be 5-micron holes with a 20-micron spacing (pitch). However, this configuration may be varied according to many factors including but not limited to drug viscosity, drug aggregate formation size, flow rate, and filter efficiency.

The flow-altering structure may be created in subsequent steps of deposition or assembled together from various subcomponents at a later step. In specific applications, the filter may be created by any of a variety of techniques. One approach is a conventional MEMS fabrication sequence. Once the tube is created, but without trimming, a patterned photoresist layer is used as an etching mask and the parylene is etched by reactive-ion etching (RIE) oxygen plasma. Alternatively, a laser-resistant mask may be created and the desired filter pattern laser drilled through the mask. An additional alternative method is mechanical drilling. According to the material of the flexible diaphragm feature, the method of filter creation may differ as known to those skilled in the art.

Figure 6A:
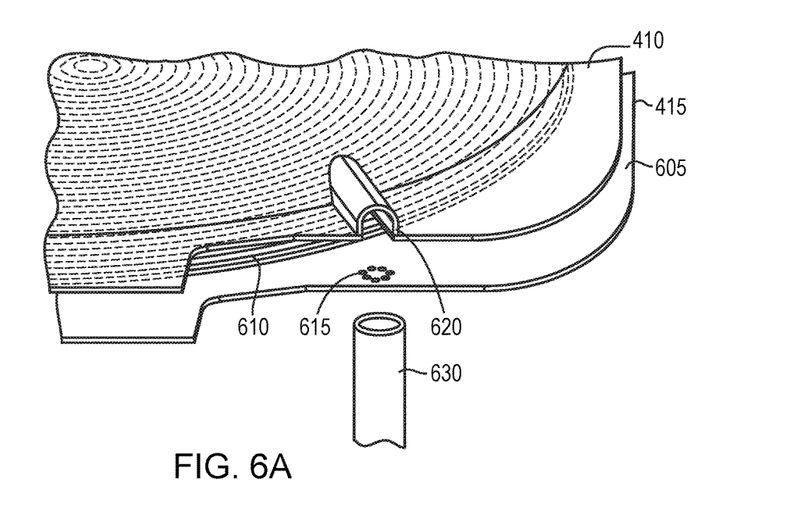
FIGS. 6A and 6B are, respectively, exploded and plan views illustrating flow-altering structure s incorporated within a structure to which a tubular conduit is bonded.
Figure 6B:
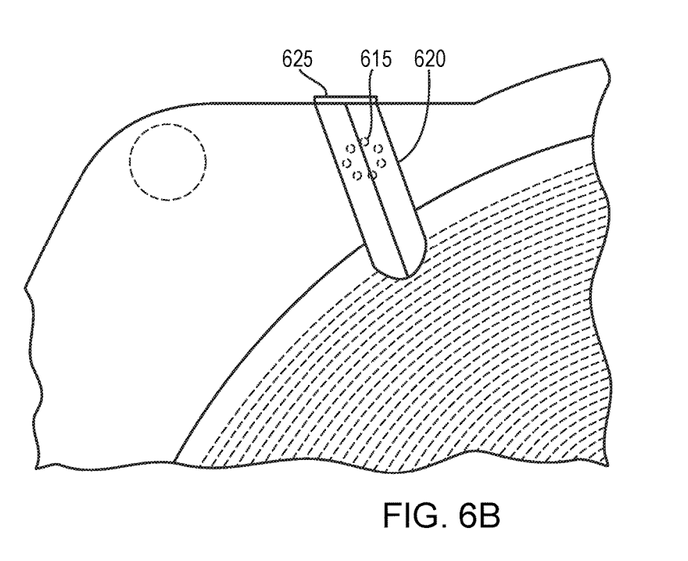

The polymeric tubing with an integrated filter may be inserted into a fluid access point in a drug pump, i.e., fluidically connected to an outlet or refill port. This allows for movement during the refill process or for normal movement of the patient. The pump may be periodically actuated to dislodge any drug aggregate or other debris trapped on the filter. Alternatively, the flow-control structure may be fabricated on a surface to which a conduit is bonded, e.g., to a wall of the drug chamber. This is illustrated in FIGS. 6A and 6B. The bottom member 415 of the drug pump includes a rigid peripheral frame 605 that surrounds the flexible diaphragm 610. A plurality of apertures 615 may be drilled, etched or otherwise fabricated through the frame 605. The apertures 615 are sized and patterned to provide a desired filter or flow-control function. To establish fluidic continuity between the apertures 615 and the drug reservoir 430 (see FIG. 4C), a raised rigid feature 620, corresponding structurally to one of the access points 420, 425 shown in FIG. 4A, is utilized. Here, however, the end face 625 of the raised feature 620 is sealed so the feature serves as a rigid conduit between the apertures 615 and the interior of the drug chamber. The end of a cannula or other conduit 630 is bonded (e.g., using an adhesive, heat, or other suitable technique) to the underside of the frame 605 so that the lumen of the conduit 630 fully surrounds the pattern of apertures. Hence, as the diaphragm 610 expands into the drug chamber, fluid is forced into the raised feature 620, passing through the apertures 615 before entering the conduit 630. The conduit 630 may connect to other components such as a flow restrictor or valve, and finally to the target tissue region.

Various embodiments of the invention are described above. It will, however, be apparent to those of ordinary skill in the art that other embodiments incorporating the concepts disclosed herein may be used without departing from the spirit and scope of the invention. Accordingly, the above description is intended to be only illustrative and not restrictive.

What is claimed is:

1. An implantable pump comprising:
   first and second walls forming a chamber therebetween, the first wall comprising (i) an expandable diaphragm so as to vary a volume of the chamber and (ii) a rigid frame surrounding the diaphragm;
   a plurality of apertures through the rigid frame;
   an ejection mechanism for selectively expanding the first wall; and
   a tubular conduit bonded to an exterior face of the rigid frame such that a lumen of the tubular conduit surrounds the apertures, actuation of the ejection mechanism forcing fluid from the chamber and through the tubular conduit via the apertures so as to filter the fluid.

2. The implantable pump of claim 1, wherein the apertures are sized to provide a target degree of filtration or a target flow alteration.

3. The implantable pump of claim 1, wherein the apertures have a diameter of about 5 microns.

4. The implantable pump of claim 1, wherein the apertures are spaced apart by about 20 microns.

5. The implantable pump of claim 1, further comprising a flow restrictor coupled to the tubular conduit.

6. The implantable pump of claim 1, further comprising a valve coupled to the tubular conduit.

7. The implantable pump of claim 1, further comprising a refill port for periodically flushing contents of the chamber and/or obstructions to the apertures.

8. The implantable pump of claim 7, wherein the refill port is molded into the second wall.

9. The pump of claim 1, further comprising a second tubular conduit having a sealed end face and bonded to an exterior face of the second wall for fluidically coupling the chamber to the apertures.

* * * * *